United States Patent [19]

Verbrugge et al.

[11] Patent Number: 4,778,577
[45] Date of Patent: Oct. 18, 1988

[54] PROCESS FOR PREPARING AZETIDINE DERIVATIVES; AND INTERMEDIATES THEREIN

[75] Inventors: Pieter A. Verbrugge; Jannetje De Waal; David W. Sopher, all of Amsterdam, Netherlands

[73] Assignee: Shell Oil Company, Houston, Tex.

[21] Appl. No.: 852,857

[22] Filed: Apr. 16, 1986

[30] Foreign Application Priority Data

Apr. 16, 1985 [GB] United Kingdom ................ 8509746

[51] Int. Cl.$^4$ ..................... B01J 19/08; C07D 205/04
[52] U.S. Cl. ......................................... 204/78; 548/953
[58] Field of Search .................. 548/953; 204/157.71, 204/78

[56] References Cited

PUBLICATIONS

Campbell, et al., Chem. Abstracts, 102, (1985), entry 122076z.
Fieser & Fieser, *Reagents for Organic Synthesis*, John Wiley & Sons (1967) pp. 731–732.
Kwart, et al., Chem. Abstracts, 90, (1979), entry 54231c.
Blum et al., *Acta. Chem. Scand.*, 338, (1981), pp. 739–741.

*Primary Examiner*—Nicholas S. Rizzo
*Assistant Examiner*—William A. Teoli, Jr.

[57] ABSTRACT

Process for the preparation of a compound of formula or a salt thereof

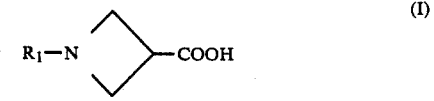

wherein $R_1$ represents a hydrogen atom or a group of formula $R_2SO_2$ or phenyl—$CH(R_3)$—wherein $R_2$ represents a phenyl, tolyl or $C_{1-4}$ alkyl group and $R_3$ represents a hydrogen atom or a phenyl of $C_{1-4}$ alkyl group, which process comprises contacting nickel in an oxidation state of at least 3 with a 3-hydroxymethyl azetidine derivative of formula

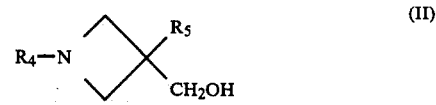

wherein $R_4$ represents a group of formula $R_2SO_2$ or phenyl—$CH(R_3)$—and $R_5$ represents a hydrogen atom or a hydroxymethyl group or a group of formula COOH or a salt thereof, followed, where $R_5$ is not a hydrogen atom, by the decarboxylation of the compound of the 3,3-dicarboxylic intermediate product or a salt thereof and, if desired to produce a compound in which $R_1$ represents a hydrogen atom, by deprotection of the N-atom. Also, novel N-substituted azetidine carboxylate derivatives of the formula

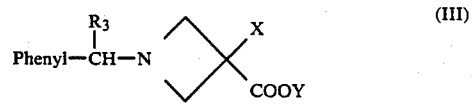

wherein X represents a group $CH_2OH$ or COOY where Y represents a hydrogen or an alkali or alkaline earth metal atom.

8 Claims, No Drawings

PROCESS FOR PREPARING AZETIDINE DERIVATIVES; AND INTERMEDIATES THEREIN

This invention relates to a process for preparing azetidine derivatives, in particular azetidine-3-carboxylic acid derivatives and salts thereof, together with certain novel compounds formed as intermediates in such process.

European Patent Application Publication No. 29265 discloses that 3-carboxyazetidine (azetidine-3-carboxylic acid) and related compounds are chemical hybridising agents, their mode of action presumably being based on their ability to produce male sterility in plants. That application also describes a process for their preparation, starting from 3-cyano-N-diphenylmethylazetidine, which may be prepared by methods known per se. Although the process described works well, it is not ideally suited for large scale preparations, since the bulky diphenylmethyl group on the nitrogen atom is removed only in the last of a series of steps, which means that in all but the last step large equipment is needed. Moreover, the apparent starting compound (diphenylmethyl)amine is relatively expensive.

Applicants' Copending UK Patent Application No. 8415615 describes a process for preparing azetidine-3-carboxylic acid by oxidising a 3,3-bis(hydroxymethyl)azetidine with nitric acid. That reaction is believed to proceed via N-nitroso azetidine intermediates. Under some circumstances it may be preferable to avoid the formation of these compounds, and in such cases an alternative oxidation technique is required. It has now been found that the requisite oxidation can be effected by means of nickel in an oxidised state.

Accordingly, the present invention provides a process for the preparation of a compound of formula

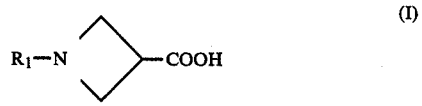

(I)

or a salt thereof, wherein $R_1$ represents a hydrogen atom or a group of formula $R_2SO_2$ or phenyl—$CH(R_3)$— wherein $R_2$ represents a phenyl, tolyl or $C_{1-4}$ alkyl group and $R_3$ represents a hydrogen atom or a phenyl or $C_{1-4}$ alkyl group, which process comprises contacting nickel in an oxidation state of at least 3 with a 3-hydroxymethyl azetidine derivative of formula

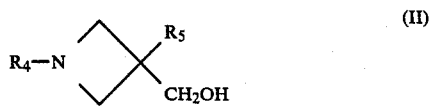

(II)

wherein $R_4$ represents a group of formula $R_2SO_2$ or phenyl—$CH(R_3)$— and $R_5$ represents a hydrogen atom or a hydroxymethyl group or a group of formula COOH or a salt thereof, followed, where $R_5$ is not a hydrogen atom, by the decarboxylation of the 3,3-dicarboxylic intermediate product or a salt thereof, and, if desired to produce a compound in which $R_1$ represents a hydrogen atom, by deprotection of the N-atom. Preferably, $R_1$ is a tosyl or benzyl group, because such groups 'protect' the nitrogen atom, in that they minimise the formation of undesired by-products from competing reactions, and also facilitate the practical manipulation of the reactants. Practical manipulation may also be facilitated by conversion between acids and salts (suitably salts of alkali metals, such as sodium and potassium, and alkaline earth metals, such as calcium, magnesium and barium). For example salts may enable easier isolation of the oxidation products to take place whilst acids may be preferred for decarboxylation.

Preferably, when desired to produce a compound in which $R_1$ represents a hydrogen atom, the deprotection step follows the decarboxylation step.

The nickel may be brought into the requisite oxidation state of at least 3 by either chemical or electrochemical means. In the former case, the reactant species is conveniently nickel peroxide, which may either be prepared separately or generated in situ by the reaction of a hypohalite with a nickel (II) salt suitably a halide. The nickel halide is suitably nickel (II) chloride, and the hypohalite is suitably an alkali metal, preferably sodium, hypochlorite or hypobromite, which itself may be generated in situ by reaction of elemental bromine or chlorine with the alkali metal hydroxide. The reaction is suitably carried out at ambient temperature (20°–30° C.).

Electrochemical oxidation of reactant II is effected by passing electrical current through an electrochemical cell having an anode with a nickel surface and containing said reactant in an aqueous, conductive medium, suitably containing an alkali hydroxide. The nickel surface of the anode may be electrochemically activated prior to the electrochemical oxidation. Procedures for such activation are well-known from the literature, one convenient technique being to pass electrical current whilst the nickel is in contact with nickel (II) ions and alkali hydroxide (as described in Trans. Faraday Soc., 1955, 51, 1433). A form of elctrochemical cell particularly advantageous for this reaction is one in which the electrodes comprise an electrode roll formed by spiralling a flexible sandwich of electrode layers and electrical insulating spacing layers, through which electrolyte may flow. Such a cell is described in J. Electroanal. Chem. 65 (1975) 883–900.

The electrochemical oxidation is suitably carried out using a voltage of 1.5 to 5.0, preferably 1.8 to 3.0 and especially 2.0 to 2.5 volts. The temperature may suitably be in the range 10° to 60° C. Successively preferred sub-ranges are 20° to 60° C., 25° to 50° C., and especially, 35° to 50° C. The use of elevated temperatures has the advantage that hydrogen evolves easily without causing foaming and that cooling can be simply effected by using water at ambient temperature. The electrolytic reaction is continued until an appropriate total charge has been passed, suitably from 6 to 12 Faraday per mole of reactant II, preferably 8 to 11, and especially 8.5 to 9.5. The reactant II may be added to the electrochemical cell at intervals but it has been determined that yield is improved if it is added in a single batch at the start of the oxidation.

The flow rate through a cell of the type described in J. Electroanal. Chem. 65 (1975), 883–900 is not critical in this application and may conveniently be in the range for example of 10 to 70 liters/hour depending on total liquid volume, and the desired temperature. The residence time of the electrolyte in such a cell may suitably be 10 to 60 seconds and would typically be 30 to 40 seconds. The electrodes may be of imperforate, sheet form or, preferably, perforate form, suitably gauze or net.

The time-average current density employed during oxidation is a matter of choice, depending upon the type of cell and the power unit employed. Gauze electrodes generally enable higher current densities to be employed. A preferred range is 100-2000 Am$^{-2}$. The current density is preferably lowered at the end of the oxidation, suitably to less than 100 Am$^{-2}$, suitably to 20-40 Am$^{-2}$, to prevent the electrolysis of water. The separate activation of the nickel surface of the anode of such a cell, when carried out, may suitably employ a current of from 1 to 10 Am$^{-2}$ but activation is especially effective if 2 to 5 Am$^{-2}$ are passed preferably for a short period, such as 10 to 20 minutes. An intermittant current may be employed.

Nickel nitrate hexahydrate is a convenient source of the nickel (II) ions required for activation and this compound may suitably be present in an amount of from 0.5 to 50.0 g/m$^2$ of anode surface, preferably exceeding 2.5 g/m$^2$.10.0 to 30.0 g.m$^2$ is an especially preferred range. Other sources of nickel (II) ions may be employed.

When an alkali hydroxide is employed in the electrochemical oxidation step it is preferably in a molar excess over the reactant II, the molar ratio suitable being from 2 to 5, and preferably being 3 to 3.5. The reactant II is preferably present in the electrolyte at a concentration of 0.25 to 1.50 mole/liter, suitably from 0.9 to 1.3 mole/liter, and preferably from 0.9 to 1.1 mole/liter.

The disodium dicarboxylate azetidine compound which is the product of electrochemical oxidation as described above may readily be worked up by removal of water and addition of a aliphatic alcohol, suitably methanol or ethanol, which causes the salt to precipitate.

When the reactant II is a compound in which $R_4$ is not a hydrogen atom the direct product of the oxidation process is the 3,3-dicarboxy azetidine derivative. This intermediate can readily be converted to the desired 3-carboxylic compound by thermal decarboxylation. The conditions for such a treatment are well known to those skilled in the art, suitably being the heating of an aqueous solution, usually under acid conditions e.g. addition of acid such as hydrochloric, formic or acetic, and conveniently at the reflux temperaure of the reaction mixture. Other techniques are also available. Decarboxylation can be effected by heating in the solid state, decarboxylation generally occuring in the melt (commonly 140°-160° C.). Preferably, a catalytic amount of a amine base such as pyridine or piperidine is added, to lower the decarboxylation temperature. Another technique is to heat the 3,3-dicarboxy-azetidine derivative in an amine base, preferably to a temperature between 80° C. and the reflux temperature. Pyridine, preferably with piperidine present, is suitable.

When a compound of formula I in which $R^1$ represents hydrogen is desired, the protecting group $R^4$ is removed. When $R^4$ represents a group of formula phenyl—CH($R_3$)— this may be effected by catalytic hydrogenation, for example using a palladium catalyst, suitably on a carrier such as charcoal, and preferably with acetic acid present. Hydrogen gas is preferably bubbled through the solution. Alternatively, instead of hydrogen gas, other hydrogen donors may be used, for example, formic acid (J. Chem. Res., (s), 1979, 108-9) or a cycloalkene such as cyclohexene (Perkins Transactions I, (1977), 490) or 1,4-cyclohexadiene (J. Org. Chem., 43, (1978), 4194). When $R^4$ represents a group of formula $R_2SO_2$, this may be removed by reaction with sodium in liquid ammonia or naphthalene, suitably in the presence of an organic solvent, or by treatment with nitric acid followed by catalytic hydrogenation of the resulting N-nitro product, or by electrochemical deprotection employing a tetraalkylammonium salt, preferably in an organic solvent. Examples of suitable electrolyte mixtures are tetramethylammonium chloride/methanol, tetramethylammonium bromide/acetonitrile and tetrabutylammonium perchlorate or tetrafluoroborate in N,N-dimethylformamide.

Certain of the 3,3-disubstituted intermediate compounds are believed to be novel compounds, namely those compounds of formula II wherein $R_4$ is carboxy or hydroxymethyl and $R_1$ is not a sulphonyl group. Accordingly, the invention includes also N-substituted-azetidine-carboxylate derivatives of the formula

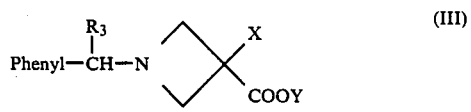

wherein $R_3$ and Y have the meanings defined above and X represents the group $CH_2OH$ or COOY where Y represents a hydrogen or alkali or alkaline earth metal atom.

The process of the invention is illustrated in the following Examples. All products were spectroscopically characterised by IR spectra in Nujol mull, and by $^1$H N.M.R. spectra.

EXAMPLE 1

Electrochemical oxidation of N-benzyl-3,3-bis(hydroxymethyl)azetidine

A 200 ml glass beaker was provided with a cylindrical nickel plate anode (4.0 cm high, 4.50 cm diameter) and a steel net cathode (4.0 cm high, 4.40 cm diameter; net specification: mesh 0.16 mm, wire thickness 0.1 mm) located within the cylindrical anode and separated from the anode by a polypropylene net cylinder (4.5 cm high, 4.45 cm diameter; net specification: mesh 0.18 mm, fibre thickness 0.15 mm). The electrolytic cell thus formed was provided with a polypropylene lid and with a magnetic stirrer bar to enable cell contents to be stirred vigorously.

150 ml of a 1.0 molar aqueous solution of sodium hydroxide was introduced into the cell and 15.5 g N-benzyl-3,3-bis(hydroxymethyl)azetidine was added and dissolved with stirring, followed by 0.5 g nickel (II) nitrate in 1 ml water.

Electrolysis was effected at 25° C. by passing a current of 0.6 A through the cell for a period of 30 hours (9F/mol. of N-benzyl-3,3-bis(hydroxymethyl)azetidine). The cell voltage remained at 1.9-2.1 v until the last F/mol (about the last 3 hours), over which the voltage increased to 2.5 v.

The electrolyte was filtered to give a pale yellow solution which was evaporated under reduced pressure to a third of its initial volume. Concentrated hydrochloric acid was added until pH 2 was reached, and the mixture was allowed to stand for 16 hours. The white solid which precipitated out was filtered off, washed with water and dried under vacuum to give N-benzylazetidine-3,3-dicarboxylic acid as a white powder (10.9 g, purity, HPLC, 92%).

The product decomposes on heating (therefore no meaningful melting point), and was characterised by the NMR spectrum of its sodium salt (see below) and its IR spectrum:
    1800–3000 cm$^{-1}$ broad absorption (OH bonds)
    1705 sharp peak (COOH)
    1640 large, broad peak (COO$^-$)
    large sharp peaks at 685, 720, 775, 810, 825, 876

Addition of sodium hydroxide to the free acid gave the disodium salt as a water-soluble white powder (no m.pt.) having the following NMR spectrum (in D$_2$O):
    7.35 ppm 5 H (s)
    3.75 ppm 2 H (s)
    3.70 ppm 4 H (s)
and the following IR Spectrum
    3620 cm$^{-1}$ sharp peak
    1600 large broad twin peak (COO$^-$)
    Sharp peaks at 780, 755 and 705.

Similarly, the dipotassium salt was prepared as a water-soluble white powder (no m.pt.) having the following IR spectrum;
    3625 cm$^{-1}$ sharp peak
    1600 large, broad peak (COO$^-$)
    Sharp peaks at 1205 (small), 1140 (small), 1080 (small), 1065 (small), 1033, 965, 945, 890, 870, 780, 752, 720

Addition of calcium or magnesium ions to a solution of the above sodium salt gave, respectively, the dibasic calcium or magnesium salts, each being a white powder, slightly soluble in water, and having the following IR Spectra:

Calcium salt:
    1550 cm$^{-1}$ large, broad peak (COO$^-$)
    1200 sharp twin
    1080 sharp
    1035 sharp twin
    Sharp peaks at 950, 880 (large), 785, 750, 720 (twin), 700

Magnesium salt 1625 and 1565 cm$^{-1}$ large, broad peaks (COO$^-$)
    Sharp peaks at 1300, 1250, 1230 (twin), 1195, 1055, 1045, 965, 925, 900, 840, 800, 765, 725, 705.

EXAMPLE 2

Electrochemical oxidation of N-benzyl-3-hydroxymethyl azetidine

A 200 ml glass beaker was provided with a planar nickel plate electrode (6.8 cm×4.7 cm) and a planar platinum plate electrode (4.8 cm×4.8 cm), both placed vertically, ca 3 cm apart. The electrolysis cell thus formed was provided with a polypropylene lid and a magnetic stirrer bar to enable the cell contents to be stirred vigorously.

Prior to activating the nickel electrode, both electrodes were washed with 2 molar aqueous hydrochloric acid and then rinsed with water. The nickel electrode was activated by a modification of a known procedure (G. W. D. Briggs, E. Jones & W. F. K. Wynne-Jones, Trans. Faraday So., 1955, 51, 1433). Thus 150 ml of an aqueous solution containing sodium acetate (0.1 molar), nickel (II) nitrate (0.05 molar) and sodium hydroxide (0.005 molar) was introduced into the cell. A current of 32 mA was passed through the cell (nickel as anode and platinum as cathode) for 10 seconds and then the electrode polarity reversed for 5 seconds. The polarity was again reversed and then the procedure repeated for a total of 5 minutes, during which time a black deposit built up on the nickel electrode. The solution was removed, the electrodes and cell rinsed with water.

150 ml of a 0.5 molar aqueous solution of sodium hydroxide was introduced into the cell and N-benzyl-3-hydroxymethylazetidine (2.0 g) was added. Electrolysis was effected at 25° C. by passing a current of 0.1 A through the cell (nickel as anode and platinum as cathode) for a period of 24.3 hours (8 F/mol. of N-benzyl-3-hydroxymethyl azetidine).

The electrolyte was extracted with diethylether (50 ml, 2 times), and the aqueous layer acidified with concentrated hydrochloric acid until a pH of 5 was attained. The solution was then evaporated to dryness under reduced pressure and the residue was washed with methanol (150 ml). Evaporation of the methanol left a beige solid (2.4 g) which was purified by ion exchange, using "Dowex 50" (trade mark) resin, to give N-benzylazetidine-3-carboxylic acid (1.33 g, 62% isolated yield).

EXAMPLE 3

Electrochemical oxidation of N-benzyl-3,3-bis-(hydroxymethyl)azetidine at 60° C.

Following a nickel anode activation step and electrolysis procedure similar to that of Example 2, N-benzyl-3,3-bis(hydroxymethyl)-azetidine (10.0 g) was oxidised in 2.0 molar aqueous sodium hydroxide at 60° C. using a current density of 14 mA cm$^{-2}$ until 12.6 F/mol of N-benzyl-3,3-bis-(hydroxymethyl)azetidine had been passed.

The electrolyte was cooled, extracted with diethylether (50 ml, 2 times) and acidified with concentrated hydrochloric acid until a pH of 2 was attained. The solution was boiled under reflux for 2 hours, then neutralised to pH7 with aqueous sodium hydroxide solution and evaporated to dryness. The solid thus obtained was stirred in boiling isopropyl alcohol and the sodium chloride removed by filtration. The isopropyl alcohol was evaporated to give N-benzylazetidine-3-carboxylic acid as a pale yellow solid (8.13 g, purity 80%, isolated yield 70%).

EXAMPLE 4

Electrochemical oxidation of N-benzyl-3,3-bis(hydroxymethyl)azetidine with a "Swiss roll" cell, followed by work-up to the disodium salt of 1-benzylazetidine-3,3-dicarboxylic acid In this experiment a "Swiss roll" electrochemical reactor was used. The construction of this cell is described in detail in J. Electroanal. Chem. 65 (1975) 885 ff. The cell was used as part of a liquid circulating loop, consisting of, respectively, a pump, a flow meter, the "Swiss roll" cell (having an anode are of 0.6 m$^2$), a heat exchanger and a stirred vessel. The vessel served to separate the hydrogen gas produced in the reactor from the liquid, and was also used to add ingredients and to measure the pH.

The cell was pretreated by circulating through it, a 0.03 molar nitric acid solution in water, followed by a solution of 25.5 g NaOH (0.64 mol) in 350 g water to which a solution of 5 mmol of Ni(NO$_3$)$_2$ had been added. While circulating the basic nickel salt solution, a current of 2 A was fed through the cell during 10 minutes. This caused precipitation on the electrode surface of most of the colloidal nickel hydroxide, formed on mixing the Ni(NO$_3$)$_2$ with the NaOH solution.

To the solution was added a solution of 43.9 g (0.21 mol) N-benzyl-3,3-bis(hydroxymethyl)azetidine in 40 g water. This was oxidized by a charge of 49 Ah (1.83 F, 8.7 F mol$^{-1}$), at a cell voltage of 2–2.5 V. The time-average current density was 33 A m$^{-2}$. The liquid circulation rate was 5 l h$^{-1}$. The temperature of the liquid varied between 20° and 30° C. Various samples taken during the reaction amounted to 10% of the original intake of starting material.

The resulting solution was extracted with ether to remove impurities (0.6 g) and then concentrated to 237 g by distilling off water at reduced pressure. To the solution 750 ml 96% ethanol was added. This caused precipitation of a white salt. After refluxing this mixture for 1 h at 85° C. and then cooling to room temperature the salt was filtered off. The filtrate was again concentrated at reduced pressure to 69 g. To this was added 400 ml of 96% ethanol. After refluxing for 1 h and then cooling to room temperature the precipitate was filtered off.

The combined precipitates after drying amounted to 46.3 g, containing 66%w of the disodium salt of N-benzylazetidine-3,3-dicarboxylic acid, according to HPLC. The yield on starting material was 57 mol %. According to nmr spectrocopy the precipitate contained no other organic material, the remaining 34% being sodium carbonate.

EXAMPLE 5

Electrochemical Oxidation of N-benzyl-3,3-bis(hydroxymethy)azetidine with a "Swiss Roll" cell, followed by work up to the disodium salt of 1-benzylazetidine-3,3-dicarboxylic acid The cell employed was a "Swiss roll" electrochemical reactor. Each electrode was of nickel gauze. The thread diameter of the gauze was 0.32 mm and the spacing of the threads, 0.8 mm. The macroscopic surface area of each electrode (that is, the summated area of its two plane surfaces) was 0.5 m$^2$. The electrodes were spaced by approximately 0.8 mm by a woven polypropylene net.

The cell was used as part of a liquid circulating loop having a pump, a flow meter, the electrochemical cell, a settler vessel to remove gas evolved in the cell, and a stirred mixing vessel. Cooling of the liquid was effected by water-fed jacketing around the settler vessel and the mixing vessel.

5.0 g of nickel nitrate hexahydrate was dissolved in 10 ml of water. 342 g of N-benzyl-3,3-bis-(hydroxymethyl)azetidine was dissolved in 700 ml of water. 232 g of sodium hydroxide was dissolved in 500 ml of water. The solutions were introduced to the mixing vessel with the addition of water, to a total volume of 1.5 l. The solution was mixed and the voltage switched on at 2.3 V. The current density was 300 Am$^{-2}$. The circulation rate was 60 liters/hour. The temperature of the solution entering the cell was 35° C. and leaving the cell, 50° C. The electrolysis continued for 1½ hours, until approximately 9.0F/mol of diol had been passed. The current density was then dropped to approximately 40 Am$^{-2}$ to convert the small remaining amount of starting material without causing undue water decomposition. The time-average current density employed during the process was approximately 250 Am$^{-2}$.

The system was drained and rinsed with water. Water was evaporated under reduced pressure until crystallisation began. Methanol was added, in a volume approximately twice that of the remaining solution, over ½ hour, at 60° C. The resulting solution was allowed to cool to ambient temperature over two hours. Coarse crystals separated out were removed by filtration, washed in methanol, and dried. Methanol and water were evaporated from the filtrate until crystallisation began. Methanol was then added in a volume approximately twice that of the remaining solution, over ½ hour, at 60° C. The resulting solution was allowed to cool at ambient temperature over two hours and the resultant crystals added to the first batch.

The combined precipitates after drying were shown to contain approximately 65% of the disodium salt of N-benzylazetidine-3,3-dicarboxylic acid, the balance being sodium carbonate. The yield on starting material was approximately 70 mol%.

EXAMPLE 6

Oxidation of N-benzyl-3,3-bis(hydroxymethyl)azetidine with pre-formed nickel peroxide (A) 10% aqueous sodium hypochlorite (150 ml) containing 32.3 g sodium hydroxide was added with stirring to nickel sulphate 6.0 aq. (100 g) in 230 ml water over ½ hours at room temperature. After a further hour, the resulting black precipitate was filtered off, washed several times with water, and then dried in a desiccator over calcium chloride. The resulting nickel peroxide contained 0.0037 g atom active oxygen per gram of product.

(B) N-benzyl-3,3-bis(hydroxymethyl)azetidine (2.1 g, 10 mmol), sodium hydroxide (1.6 g, 40 mmol) and water (30 ml) were stirred together at ambient temperature (20° C.). Stirring was continued during addition of the above nickel peroxide (22 g), for a total of 24 hours. Nickel hydroxide separated out as a green precipitate and was filtered off to leave a yellow-tinted aqueous solution which was evaporated to dryness under reduced pressure. The solid residue was shown by high performance liquid chromatography to contain greater than 80%w of N-benzyl-azetidine-3,3-dicarboxylic acid, disodium salt.

EXAMPLE 7

Oxidation of N-benzyl-3,3-bis(hydroxymethyl)azetidine with in situ nickel peroxide Bromine (10.6 g) was slowly added at 20° C. over 8 hours to a mixture of N-benzyl-3,3-bis(hydroxymethyl)azetidine (2.1 g) in water (50 ml) containing sodium hydroxide (9.3 g) and nickel chloride 6.0 aq. (1.5 g). After stirring overnight, the green precipitate of nickel hydroxide was filtered off, and the filtrate evaporated to dryness. The residue was boiled in ethanol, and the insoluble material (desired product as sodium salt and sodium bromide) separated and worked up to yield the N-benzyl-azetidine-3,3-dicarboxylic acid.

EXAMPLE 8

Oxidation of N-tosyl-3,3-bis(hydroxymethyl)azetidine with in situ nickel peroxide Sodium hydroxide (6.3 g) was dissolved in water (50 ml) and nickel chloride (1 g) and N-tosyl-3,3-bis(hydroxymethyl)azetidine (4.4 g) were added. Bromine (9.6 g) was added over 6 hours to the green suspension with vigorous stirring and cooling. The mixture was stirred overnight and the last traces of nickel peroxide destroyed with sodium sulphite. The green precipitate was filtered off and the clear filtrate acidified to pH 1 with hydrochloric acid. Ether extraction yielded the desired product, N-tosylazetidine-3,3-dicarboxylic acid.

EXAMPLE 9

Generation of nickel peroxide with chlorine

Following a procedure similar to that of Example 8 above, but replacing the bromine with chlorine, a clear filtrate of product was obtained after removal of green precipitate. This filtrate was boiled down, ethanol (50 ml) added. The precipitated sodium salts were filtered off, taken up in water (25 ml) and acidified with 36% HCl to pH1 to give a white precipitate of N-tosylazetidine-3,3-dicarboxylic acid.

EXAMPLE 10

Generation of nickel peroxide with sodium persulphate

Following a procedure similar to that of Example 8 above, but replacing the bromine with sodium persulphate ($Na_2S_2O_8$, 20 g), there was obtained a mixture of N-tosylazetidine-3,3-dicarboxylic acid, and N-tosyl-3-hydroxymethyl-3-carboxy azetidine.

EXAMPLE 11

Oxidation of N-benzyl-3-hydroxymethyl azetidine with in situ nickel peroxide Sodium hydroxide (1.7 g) and nickel chloride (0.35 g) were dissolved in water (20 ml). N-benzyl-3-hydroxymethyl azetidine (1.06 g) was dissolved in dioxan (10 ml), and the two solutions mixed to yield a milky emulsion. Bromine (2 g) was added dropwise over 4 hours of 20° C., and after stirring for a further 3 hours the excess nickel peroxide was destroyed with sodium sulphite and the precipitate filtered off.

The clear filtrate was first acidified to pH3 and extracted and ether, then neutralised to pH7 with sodium hydroxide and the solution boiled to dryness. N-benzyl azetidine-3-carboxylic acid was recovered from the salt residues.

EXAMPLE 12

Preparation of N-benzylazetidine-3,3-dicarboxylic acid from the crude disodium salt A portion of 49.3 g crude disodium salt of N-benzylazetidine-3,3-dicarboxylic acid, prepared according to the method given in Example 4, purity 72.6%, corresponding to 128 mmol, was dissolved in 150 ml of water. This solution was acidified at room temperature by adding slowly (1 h) concentrated hydrochloric acid (36%) until a pH of 1.5 was reached. The precipitate was filtered, washed with water, and dried, to give 27.3 g of N-benzylazetidine-3,3-dicarboxylic acid of 100% purity according to HPLC. Molar yield 91% on the disodium salt.

EXAMPLE 13

Preparation of N-alpha methylbenzylazetidine-3,3-dicarboxylic acid by oxidation with in situ nickel peroxide (A) 2,2-bis(bromomethyl)-propan-1,3-diol (104.3 g) and acetone (34.8 g) dissolved in petroleum ether (62/82; 150 cc), p. toluenesulphonic acid (0.4 g) added, and the reaction mixture refluxed for 4½ hr over a Dean Stark water separator. The petroleum ether solvent and excess acetone were distilled off, and sodium carbonate (42.5 g) and xylene (20 cc) were added to the acetal product, followed by dl-alpha methyl benzylamine (48.5 g), sodium hydroxide (33.5 g) and xylene (60 cc). This mixture was boiled with vigorous stirring over a Dean Stark water separator, and some xylene distilled off to reach a reaction temperature of 160° C. After 62 hr. the mixture was cooled to about 50° C., further xylene added, the solid residues filtered off and the filtrate washed with water. The xylene phase was then washed with small portions of 20% hydrogen chloride solution until the water layer remained acidic. The combined HCl extracts were basified to pH 12.4 under vigorous stirring with solid sodium hydroxide. The white solid was filtered off, washed and dried to yield N-alpha methylbenzyl-3,3-bis(hydroxymethyl)-azetidine, having the following NMR spectrum (in $CDCl_3$—$CD_3OH$):

7.18 ppm 5 H (s)
3.3 ppm 1 H (m)
3.65 ppm 4 H (s)
2.95 ppm 4 H (m)
1.15 ppm 3 H (d)

(B) Sodium hydroxide (12.6 g) and nickel chloride (2.0 g as hydrate) were dissolved in water (100 cc), and the diol product of A (6.63 g) added. Bromine (20.5 g) was added dropwise at 25° C. with vigorous stirring over a 4 hr. period. The mixture was stirred overnight (15 hr), when the black colour changed to green. The precipitated nickel hydroxide was filtered off, and the residue worked up to yield the disodium salt of N-alpha methylbenzyl azetidine-3,3-dicarboxylic acid as a water-soluble white powder (no m.pt.) having the following NMR spectrum (in $D_2O$):

7.40 ppm 5 H (s)
1.25 ppm 3 H (d)
3.5 ppm 5 H (m)

The IR spectrum had the following peaks:
1620 $cm^{-1}$ large broad ($COO^-$)
1380 (small), 1340 (small), 1205 (small), 1145, 805 (small), 765, 705.

The free acid was also prepared by dissolving the disodium salt in water and acidifying with HCl to pH 1.8. This product had the following IR spectrum peaks:
1800–2800 $cm^{-1}$ broad (OH)
1730 (COOH)
1600 large, broad ($COO^-$)
855, 767, 710, 662

EXAMPLE 14

Following a procedure similar to that of Example 13, N-benzhydryl-azetidine-3,3-dicarboxylic acid was prepared, having the following NMR spectrum ($D_2O$+-NaOH):

7.25 ppm 10 H (m)
4.4 ppm 1 H (s)
3.5 ppm 4 H (s)

EXAMPLE 15

Preparation of N-benzyl-3-hydroxymethyl-azetidine-3-carboxylic acid by electrolytic oxidation An 800 ml glass beaker was provided with a cylindrical nickel net anode (13.5 cm high, 8 cm diameter; net specification: mesh 0.16 mm, wire thickness 0.1 mm) and a centrally placed stainless steel rod cathode (2 cm diameter). The electrolysis cell thus formed was provided with a Teflon lid and magnetic stirrer bar to enable the cell contents to be stirred vigorously.

Following a nickel anode activation step similar to that of Example 2, the cell was charged with 100 ml of a 1.0 molar aqueous solution of sodium hydroxide and N-benzyl-3,3-bis-(hydroxymethyl)-azetidine (20.7 g) added. The electrolysis was carried out at 25° C. by passing a current of 0.62 A through the cell (nickel as anode, steel as cathode) for a period of 6.0 hours followed by passing a current of 3.5 A (same electrode polarity) for a period of 5.0 hours (total of 8 F/mol of N-benzyl-3,3-bis-(hydroxymethyl)-azetidine).

The electrolysis product was worked up by flashing off most of the water, to leave about 60 g of a semisolid residue which was boiled up in 200 ml ethanol. After cooling, the solid was filtered off to yield N-benzyl-azetidine-3,3-dicarboxylic acid, disodium salt. The ethanol filtrate was evaporated and the residual solution of concentrated alkali stirred with tetrahydrofuran (200 ml), which yielded a white solid at the interface between a yellow upper layer and a colourless aqueous layer. This solid was recovered over a glass filter and washed with tetrahydrofuran to yield the sodium salt of N-benzyl-3-hydroxymethyl-azetidine-3-carboxylic acid.

This salt was dissolved in water, the insoluble impurities filtered off, acidified to pH2 with hydrochloric acid and extracted with ether. The product was then neutralised (pH7) with sodium bicarbonate, and the aminohydroxy acid separated from inorganics by standard procedures to yield 5 g of a white solid identified as N-benzyl-3-hydroxymethyl-azetidine-3-carboxylic acid, having the following spectral characteristics:

| NMR | 7.50 ppm 5 H (s) |
|---|---|
| (D$_2$O) | 4.35 ppm 2 H (s) |
| | 4.20 ppm 2 H (s) |
| | 4.12 ppm 2 H (s) |
| | 3.72 ppm 2 H (s) |

IR peaks at 3250 (large, broad), 1800–2800 (broad; OH bands), 1620 (large, broad COO$^-$), 1060 (large, sharp), 880, 760, 705.

EXAMPLE 16

Conversion of N-benzyl-azetidine-3,3-dicarboxylic acid to N-benzyl-azetidine-3-carboxylic acid A mixture of N-benzyl-azetidine-3,3-dicarboxylic acid (6.0 g, 25 mmol) and acetic acid (60 g) was heated to 95° C. with stirring. This caused evolution of CO$_2$, and dissolution of the solid. After 1 h at 95° C. the gas evolution had stopped, and nmr analysis showed that decarboxylation to N-benzyl-azetidine-3-carboxylic acid was complete.

EXAMPLE 17

Conversion of disodium salt of N-benzylazetidine-3,3-dicarboxylic acid to N-benzyl-3-carboxyazetidine A mixture of the disodium salt of N-benzylazetidine-3,3-dicarboxylic acid and sodium carbonate (approximately 2:1 by weight, total weight 7.5 g) were dissolved in 100 ml of a toluene-acetic acid mixture (2/1, v/v), with immediate evolution of carbon dioxide from the sodium carbonate. The mixture was warmed and stirred, and then refluxed over a Dean and Stark water separator. After ½ hour evolution of carbon dioxide had ceased and 1.5 ml of an acetic acid-water mixture had separated. The slightly hazy solution was cooled to room temperature. A white fluffy solid comprising sodium acetate (3.6) g) was removed by filtration. Distillation of the clear filtrate yielded 4.5 g of N-benzyl-3-carboxy-azetidine.

EXAMPLE 18

Conversion of N-benzyl-azetidine-3-carboxylic acid to azetidine-3-carboxylic acid The solution of N-benzylazetidine-3-carboxylic acid produced by Example 16 was cooled to 50° C., and 0.6 g of a palladium on charcoal catalyst (containing 10%w of palladium) was added. Hydrogen at atmospheric pressure was then bubbled through for 3 h. Nmr spectrosopy showed that the hydrogenolysis was complete at this point. The catalyst was filtered off, and the filtrate was concentrated at reduced pressure until crystals began to form. By adding isopropanol (50 ml) the product was precipitated. Filtration and drying of the precipitate gave 2.39 g of azetidine-3-carboxylic acid, purity 97.4%w by HPLC, corresponding to a 93% yield on N-benzylazetidine-3,3-dicarboxylic acid of Example 16.

EXAMPLE 19

Conversion of N-tosylazetidine-3-carboxylic acid to azetidine 3-carboxylic acid

A 100 ml, waterjacketed, beaker cell was provided with a mercury pool cathode of approximate area 10 cm$^2$ and, parallel to the cathode, a platinum coil anode, contained in a glass anode compartment (volume 10 ml) and separated from the catholyte by a porous sintered glass disc. The potential of the cathode was controlled by means of a luggin capillary (the tip of which was placed 1-2 mm away from the mercury pool) and a saturated calomel electrode. Air was excluded from the cathode compartment by passing nitrogen continuously through the catholyte. The electrolysis cell thus formed was provided with a polypropylene lid and a magnetic stirring bar to enable the mercury pool and contents of the cathode compartment to be stirred.

Both cathode and anode compartments and the luggin capillary were filled with 0.1 molar tetra-n-butylammonium tetrafluoroborate in N,N-dimethylformamide. N-Tosylazetidine-3-carboxylic acid (1.0 g) was added to the cathode compartment. The electrolysis was carried out at approximately 15° C., maintaining the cathode potential at $-2.2$ V for 650 coulombs (1.5 F/mole of N-tosylazetidine-3-carboxylic acid) and then at $-2.5$ V for a further 650 coulombs.

The catholyte was removed from the cell and the N,N-dimethylformamide distilled off under high vacuum to leave approximately 5 ml of yellow solution. Glacial acetic acid (0.2 ml) was added and the precipitated solid collected by filtration. Analysis of this material by n.m.r. spectroscopy and thin layer chromatography indicated that it was predominantly azetidine-3-carboxylic acid (0.09 g, 25% yield).

EXAMPLE 20

Conversion of N-tosylazetidine-3-carboxylic acid to azetidine-3-carboxylic acid

N-tosylazetidine-3-carboxylic acid (2.0 g) was suspended in water (20 ml) and neutralised (pH 7-8) with 20% aqueous tetraethylammonium hydroxide. The water was removed under reduced pressure to leave a white solid (3.0 g, 100% yield).

A portion (1.0 g) of this material was added to the electrolysis cell described of Example 19, filled with the same solvent and supporting electrolyte. The electrolysis was carried out at about 20° C., maintaining the cathode potential at −2.5 V for a total of 550 coulombs (1.8 F/mole tetraethylammonium N-tosylazetidine-3-carboxylate). By following the same product isolation procedure as described in Example 19, azetidine-3-carboxylic acid was obtained (0.17 g, 54% yield on N-tosylazetidine-3-carboxylic acid.

EXAMPLE 21

Conversion of N-tosylazetidine-3-carboxylic acid to azetidine-3-carboxylic acid

N-tosylazetidine (12 g) was stirred in aqueous 65% nitric acid (180 ml), for 2½ hours whilst the temperature was allowed to rise from −30° C. to ambient temperature. Water was removed by distillation and the resulting solid dissolved in water and extracted with ethyl acetate, to produce 7.3 g of N-nitroazetidine-3-carboxylic acid. 0.5 g of 5% palladium on charcoal catalyst was suspended in 10 ml of methanol containing 4.4% formic acid. 0.5 g of the N-nitroazetidine-3-carboxylic, dissolved in 10 ml of the same solution, was slowly added. The temperature of the solution rose and a gas was evolved. After the reaction mixture had subsided the catalyst was filtered off, and the solvent removed by distillation, leaving 0.33 g of azetidine-3-carboxylic acid.

EXAMPLE 22

Conversion of N-tosylazetidine-3-carboxylic acid to azetidine-3-carboxylic acid 1.45 g metallic sodium was added to a solution of 6 g naphthalene in 50 ml of 1,2-Ethanediol-dimethylether. After 2 hours the metal had been converted into a dark green complex and 3.8 g of N-tosylazetidine-3-carboxylic acid was added, over ½ hour, whilst the temperature was kept below 30° C. The reaction mixture was stirred for 2 hours and the colour changed to orange-brown. Boiling off the solvent yielded a mixture containing 3-carboxylic acid sodium salt and acidification by aqueous hydrogen chloride followed by extraction with diethyl ether produced an aqueous solution of azetidine-3-carboxylic acid.

We claim:

1. A process for the preparation of a compound of formula

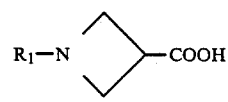

or a salt thereof, wherein $R_1$ represents a hydrogen atom or a group of formula $R_2SO_2$ or phenyl—CH($R_3$)— wherein $R_2$ represents a phenyl, tolyl or $C_{1-4}$ alkyl group and $R_3$ represents a hydrogen atom or a phenyl or $C_{1-4}$ alkyl group, which process comprises the steps of contacting nickel in an oxidation state of at least 3 with a 3-hydroxymethyl azetidine compound of formula II

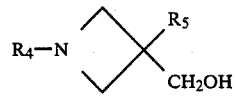

wherein $R_4$ represents a group of formula $R_2SO_2$ or phenyl—CH($R_3$)— and $R_5$ represents a hydrogen atom or a hydroxymethyl group or a group of formula COOH, or a salt thereof, followed, where $R_5$ is not a hydrogen atom, by the decarboxylation of the 3,3-dicarboxylic intermediate product or a salt thereof and, if desired to produce a compound in which $R_1$ represents a hydrogen atom, by deprotection of the N-atom.

2. A process according to claim 1 wherein $R_1$ is a tosyl or benzyl group.

3. A process according to claim 2 wherein the nickel in the required oxidation state 3 is present in the form of nickel peroxide.

4. A process according to claim 3 wherein the nickel peroxide is generated chemically in situ by reaction between an alkali metal hypohalite and a nickel (II) salt.

5. A process according to claim 1 wherein the nickel in the required oxidation state 3 is a nickel surfaced anode of an electrochemical cell.

6. A process according to claim 5 wherein the anode nickel surface is activated by passing electrical current whilst the nickel is in contact with nickel (II) ions and alkali metal hydroxide.

7. A process according to claim 6 wherein the electrical charge passed is between 6 and 12 Faradays per mole of reactant II.

8. A process according to claim 1 wherein, when $R_4$ is a carboxy or hydroxymethyl group, the intermediate 3,3-dicarboxylic product is decarboxylated by heating under acid conditions.

* * * * *